(12) United States Patent
Qiao et al.

(10) Patent No.: US 10,792,355 B2
(45) Date of Patent: Oct. 6, 2020

(54) METHOD FOR PURIFYING AND CONCENTRATING INACTIVATED ANTIGEN OF FOOT-AND-MOUTH DISEASE VIRUS

(71) Applicant: JIANGSU ACADEMY OF AGRICULTURAL SCIENCES, Nanjing (CN)

(72) Inventors: Xuwen Qiao, Nanjing (CN); Qisheng Zheng, Nanjing (CN); Xiaoming Yu, Nanjing (CN); Jin Chen, Nanjing (CN); Pengcheng Li, Nanjing (CN); Yuanpeng Zhang, Nanjing (CN); Liting Hou, Nanjing (CN); Jibo Hou, Nanjing (CN)

(73) Assignee: JIANGSU ACADEMY OF AGRICULTURAL SCIENCES, Nanjing (CN)

( * ) Notice: Subject to any disclaimer, the term of this patent is extended or adjusted under 35 U.S.C. 154(b) by 0 days.

(21) Appl. No.: 16/310,384

(22) PCT Filed: Jul. 28, 2017

(86) PCT No.: PCT/CN2017/094857
§ 371 (c)(1),
(2) Date: Dec. 14, 2018

(87) PCT Pub. No.: WO2018/137323
PCT Pub. Date: Aug. 2, 2018

(65) Prior Publication Data
US 2019/0240313 A1    Aug. 8, 2019

(30) Foreign Application Priority Data

Jan. 26, 2017 (CN) .......................... 2017 1 0062982

(51) Int. Cl.
*A61K 39/135* (2006.01)
*A61K 39/12* (2006.01)
*C07K 14/005* (2006.01)

(52) U.S. Cl.
CPC ............ *A61K 39/135* (2013.01); *A61K 39/12* (2013.01); *C07K 14/005* (2013.01); *C12N 2770/32134* (2013.01); *C12N 2770/32151* (2013.01)

(58) Field of Classification Search
None
See application file for complete search history.

(56) References Cited

PUBLICATIONS

Mandi SE, Hassanian AI, Ei-Din WMG, Ibrahim EE, Fakhry HM (2015) Validation of γ-radiation and ultraviolet as a new inactivators for foot and mouth disease virus in comparison with the traditional methods, Veterinary World 8(9): 1088-1098.*

Cheng et al., Development of GEM-PA-nanotrap for purification of foot-and-mouth disease virus, 2019, Vaccine, vol. 37, pp. 3205-3213.*

* cited by examiner

*Primary Examiner* — Benjamin P Blumel
(74) *Attorney, Agent, or Firm* — CBM Patent Consulting, LLC (57) ABSTRACT

A method for inactivated foot-and-mouth disease virus antigen purification and concentration, which relates to the field of biotechnology which includes the following steps of: (1) adding an adaptor protein with an amino acid sequence as shown in SEQ ID NO: 2 into the inactivated foot-and-mouth disease virus antigen, mixing evenly, and incubating; (2) adding a purified carrier, mixing evenly, and incubating the mixture, the purified carrier being a *Lactococcus lactis* skeleton; and (3) centrifuging and obtaining a precipitate.

9 Claims, 6 Drawing Sheets

Specification includes a Sequence Listing.

Antibody level of inactivated Asia1-type FMDV

Fig.8

Antibody level of inactivated Asia1-type FMDV

Fig.9

Antibody level of inactivated O-type FMDV

METHOD FOR PURIFYING AND CONCENTRATING INACTIVATED ANTIGEN OF FOOT-AND-MOUTH DISEASE VIRUS

TECHNICAL FIELD

The present invention relates to the field of biotechnology, and more particularly, to a method for purifying and concentrating inactivated foot-and-mouth disease virus antigen.

BACKGROUND

Foot-and-mouth disease (FMD) is an acute, febrile and highly contagious disease caused by a foot-and-mouth disease virus antigen (FMDV), mainly affecting cloven-hoofed animals such as pig, cattle, sheep and camel. At present, seven serotypes including O, A, C, SAT1, SAT 2, SAT 3 and Asia1 have been found without cross-protection among the serotypes, which increases the difficulty of prevention and control of the FMD. Once the FMD outbursts, it will bring serious economic losses to the breeding industry, and the FMD is listed as a notifiable disease by the International Epizootic Office (OIE) and is an A-class disease to be prevented and controlled in China. In China, the disease is mainly controlled by immunizing inactivated vaccine. China's FMD vaccines have been produced on a large scale, but most of the FMD vaccines are crude vaccines with low antigen content, and the content of heterologous protein (cell protein, bovine serum protein, non-structural protein, endotoxin) is over 95%, which leads to serious side effects in large-scale vaccination and has affected the prevention and control of FMD.

In order to solve the problems of insufficient antigen content and low purity in inactivated FMDV vaccine, traditional concentration and purification method currently used in production is a physical purification technology such as a membrane filtration clarification technology cooperated with a hollow fiber concentration technology. This technology can concentrate the antigen to a certain extent, remove some foreign proteins, and improve the purity and content of the vaccine antigen, but it has the defects of complex operation, high requirement on technical equipment, high purification and concentration cost, low antigen recovery rate and concentration multiple, and small amount of foreign proteins removed from the antigen, etc.

SUMMARY

Object of the present invention: the object of the present invention is to provide a method for purifying and concentrating inactivated foot-and-mouth disease virus antigen which can efficiently purify the inactivated foot-and-mouth disease virus antigen and efficiently remove impurities, and has a high antigen recovery efficiency, large concentration multiple, low equipment requirement, simple operation, and low cost.

Technical solutions: the object of the present invention is achieved by adopting the following technical solutions:

A method for purifying and concentrating inactivated foot-and-mouth disease virus antigen includes, but is not limited to the following steps of:

(1) adding an adaptor protein with an amino acid sequence as shown in SEQ ID NO: 2 into the inactivated foot-and-mouth disease virus antigen, mixing evenly, and incubating;

(2) adding a purified carrier, mixing evenly, and incubating the mixture, the purified carrier being a *Lactococcus lactis* skeleton; and (3) centrifuging and obtaining a precipitate.

In the present invention, the incubating conditions in step (1) are as follows: oscillation is conducted during an incubating process, an incubating temperature is 20 to 25° C., and an incubating time is 45 min to 60 min.

In the present invention, the incubating conditions in step (2) are as follows: oscillation is conducted during an incubating process, an incubating temperature is 20 to 25° C., and an incubating time is 25 min to 35 min.

In a preferred technical solution, an adding ratio of the adaptor protein includes, but is not limited to the following amount: 40 to 60 μg adaptor protein is added into $10^{8.7}$ $TCID_{50}$-$10^{9.2}$ $TCID_{50}$ inactivated foot-and-mouth disease virus antigen.

In a preferred technical solution, an adding ratio of the purified carrier includes, but is not limited to the following amount: $2.4*10^9$ to $2.6*10^9$ purified carriers are added into $10^{8.7}$ $TCID_{50}$-$10^{9.2}$ $TCID_{50}$ inactivated foot-and-mouth disease virus antigen.

In the present invention, the adaptor protein includes, but is not limited to being obtained through induced expression of a recombinant strain carrying a coding gene of the adaptor protein.

In the present invention, the recombinant strain includes, but is not limited to being obtained through inserting the coding gene of the adaptor protein into an expression vector pET32 with Nde I and Xho I enzyme digestion sites, and then transforming into *E. coli* bacillus.

In the present invention, the recombinant strain is cultured for 1 to 2 h under 35 to 37° C., 2 to 4 h under 24 to 26° C., and stood for 10 to 20 min under 15 to 17° C., and then isopropyl thiogalactoside with a final concentration of 0.1 to 0.3 mmol/L is added to inductively culture the mixture for 18 to 22 h under 15 to 17° C., so as to obtain the adaptor protein.

In the present invention, the *Lactococcus lactis* skeleton includes, but is not limited to being obtained through boiling the *Lactococcus lactis* with hydrochloric acid and washing.

The present invention further provides an inactivated foot-and-mouth disease virus antigen vaccine, including but not limited to containing the precipitate obtained through the method above.

Compared with the Prior Art, the Present Invention has the Following Beneficial Effects:

In the method for purifying and concentrating an inactivated foot-and-mouth disease virus antigen of the present invention, since the adaptor protein can specifically bind to the inactivated foot-and-mouth disease virus antigen and the *Lactococcus lactis* skeleton, the inactivated foot-and-mouth disease virus antigen enriched by precipitation can be harvested by a simple centrifugation step. Therefore, method of the present invention can efficiently purify the inactivated foot-and-mouth disease virus antigen, remove impurities efficiently, and has a high antigen recovery efficiency, large concentration multiple, low equipment requirement, simple operation, and low cost. The method of the present invention has a recovery efficiency of the inactivated foot-and-mouth disease virus antigen higher than 99%, and a removal efficiency of the non-antigen protein higher than 90%, and the obtained antigen is easy to preserve and prepare the foot-and-mouth disease polyvalent vaccines.

BRIEF DESCRIPTION OF THE DRAWINGS

FIG. 5A is an SDS-PAGE electrophoresis identification result, lane 1 is a supernatant 3, M is a pre-dyed standard protein molecular weight, lane 2 is an unpurified inactivated O-type FMDV antigen control, and lane 3 is a precipitate 3.

FIG. 5B is a Western-blot identification result, lane 1 is a precipitate 3, M is a pre-dyed standard protein molecular weight, lane 2 is a supernatant 3, and lane 3 is an unpurified inactivated 0-type FMDV antigen control.

FIG. 6A is an SDS-PAGE electrophoresis identification result, lane 1 is a supernatant 4, M is a pre-dyed standard protein molecular weight, lane 2 is a supernatant, and lane 3 is an unpurified Inactivated A-type FMDV antigen control.

FIG. 6B is a Western-blot identification result, lane 1 is a precipitate 4, M is a pre-dyed standard protein molecular weight, lane 2 is a supernatant 4, and lane 3 is an unpurified Inactivated A-type FMDV antigen control.

FIG. 7A is a SDS-PAGE electrophoresis identification result, lane 1 is an unpurified inactivated Asia1-type FMDV antigen view control, M is a pre-dyed standard protein molecular weight, lane 2 is a precipitate 5, and lane 3 is a supernatant 5.

FIG. 7B is a Western-blot identification result, M is a precipitate 5, M is a pre-dyed standard protein molecular weight, lane 2 is a supernatant 5, and lane 3 is an unpurified inactivated Asia1-type FMDV antigen control.

DETAILED DESCRIPTION

First Embodiment Construction and Identification of Recombinant Expression Strain PFL/BL21

An adaptor protein was designed, wherein an amino acid sequence of the adaptor protein was as shown in SEQ ID NO:2. The adaptor protein was a fusion protein containing two function identification regions, which could specifically identity an inactivated foot-and-mouth disease virus antigen and a *Lactococcus lactis* skeleton respectively. A coding gene sequence of the adaptor protein was shown in SEQ ID NO: 1. In order to facilitate the identification of the adaptor protein, six His-tag proteins (SEQ ID NO: 4: HHHHHH) were added to a carboxy terminus of the sequence shown in SEQ ID NO: 2, and a gene sequence coding the His-tag protein was added before the stop codon at a 3'-termination codon of the sequence shown in SEQ ID NO: 1. Further, Nde I and Xho I enzyme digestion sites were designed at the 5'-termination and a 3'-termination of the gene sequence shown in SEQ ID NO: 3 respectively, and sent to GenScript for synthesis. A synthesized gene fragment was inserted into a pUC57 vector to obtain a recombinant plasmid pUC-PFL.

Double enzyme digestion was conducted to the recombinant plasmid pUC-PFL and a prokaryotic expression vector pET32a by using restriction enzymes Nde I and Xho I. An enzyme digestion system was as follows:

pUC-PFL and pET32a plasmid double enzyme digestion system (30 μL):
10*Q.cut Buffer 3 μL,
Q.cut Nde I 1 μL,
Q.cut Xho I 1 μL,
pUC-PFL or pET32a plasmid 8 μL, and
dH$_2$O made up the volume to 30 μL.
10*Q.cut Buffer, Q.cut Nde I (Article No. 1621) and Q.cut Xho I (Article No. 1635) were purchased from Dalian TaKaRa.

The double enzyme digestion system was mixed evenly and then placed at 37° C. for 30 min. Bands were separated by agarose gel electrophoresis and then gel was cut. According to the instructions of an AXYGEN gel recovery kit, a target fragment PFL and a vector fragment pET32a were recovered respectively and ligated by a T4 ligase.

A T4 ligase ligation system was as follows (25 μL):
10×T4 ligase Buffer 2.5 μL,
Target fragment PFL 12 μL,
Vector fragment 3 μL,
T4 DNA ligase 1 μL, and
dH$_2$O made up the volume to 25 μL.

The above-mentioned ligation system was placed at 16° C., and ligated for 12 to 16 h, to obtain a ligation product.

Figure 1:
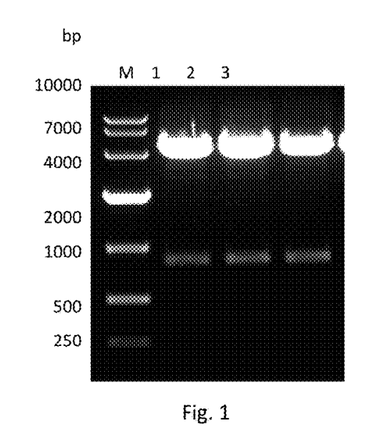
FIG. 1 is an enzyme digestion identification result of a recombinant expression plasmid pET-PFL, wherein M is a DNA standard molecular weight, and lanes 1, 2 and 3 are double enzyme digestion products of Nde I and Xho I of the recombinant expression plasmid pET-PFL.

The above ligation product was transformed into *E. coli* BL21 competent cells, and coated with LB tablets containing 50 mg/mL ampicillin, and the cells were stood at 37° C. and cultured overnight, and monoclonal cells were selected and inoculated with a LB liquid medium containing 50 mg/mL ampicillin and cultured overnight. Plasmids were extracted according to the instructions of an AXYGEN plasmid extraction kit, identified by double enzyme digestion of Q.cut Nde I and Q.cut Xho I, and an enzyme-digested product was electrophoresed to obtain FIG. 1. It could be seen from FIG. 1 that after the double enzyme digestion of positive recombinant plasmids, two bands of 5389 bp and 981 bp were obtained, and a successfully identified positive recombinant plasmid was named pET-PFL, and a positive recombinant strain was named PFL/BL21. Meanwhile, a control of transforming the pET32a plasmid into a BL21 (DE3) was set to obtain a control strain pET/BL21.

Second Embodiment Induced Expression 1 of Adaptor Protein

1. Induced Expression of Recombinant Expression Strain PFL/BL21

(1) Monoclonal strains of the strain PFL/BL21 and the control strain pET/BL21 were selected, respectively inoculated with a LB liquid medium containing 50 mg/mL ampicillin, and cultured overnight at 37° C. and 200 rpm to obtain a mother liquid.

(2) The mother liquid of each of the above strains was inoculated to a fresh LB liquid medium (containing 50 mg/mL ampicillin) at a ratio of 1:200, cultured at 35° C. and 180 rpm for 1 h, cultured at 24° C. and 180 rpm for 2 h, then stood at 15° C. for 10 min to obtain a culture.

(3) IPTG (isopropyl-beta-D-thiogalactopyranoside) at a final concentration of 0.1 mmol/L was added to the culture obtained in the step (2) for protein induction at an induction temperature of 15° C. for a culture time of 18 h, to obtain an induced strain liquid.

Third Embodiment Induced Expression 2 of Adaptor Protein

1. Induced Expression of Recombinant Expression Strain PFL/BL21

(1) Monoclonal strains of the strain PFL/BL21 and the control strain pET/BL21 were selected, respectively inoculated with a LB liquid medium containing 50 mg/mL ampicillin, and cultured overnight at 37° C. and 200 rpm to obtain a mother liquid.

(2) The mother liquid of each of the above strains was inoculated to a fresh LB liquid medium (containing 50 mg/mL ampicillin) at a ratio of 1:200, cultured at 37° C. and 180 rpm for 2 h, cultured at 25° C. and 180 rpm for 3 h, then stood at 16° C. for 15 min to obtain a culture.

(3) IPTG (isopropyl-beta-D-thiogalactopyranoside) at a final concentration of 0.2 mmol/L was added to the culture obtained in the step (2) for protein induction at an induction temperature of 16° C. for a culture time of 18 h, to obtain an induced strain liquid.

Fourth Embodiment Analysis for the Expression of Adaptor Protein (1) The induced culture in the second embodiment and the third embodiment above were separately collected, and centrifuged at 8000 g and 4° C. for 10 min to obtain cells, and then the cells were washed twice with a PBS buffer (pH 7.0 to 7.4, 0.1 mol/L), and resuspended in PBS to obtain a cell suspension.

(2) The cell suspension was subjected to high pressure cracking at 4° C. under the cracking condition of cracking for 3 to 5 cycles under a pressure of 800 MPa to obtain a cell lysate;

(3) The cell lysate was centrifuged at 12000 rpm for 15 min at 4° C., and a supernatant and a precipitate of the lysate were separately collected, and the precipitate was resuspended by a PBS buffer as the same volume as the supernatant.

All the above operations were carried out in a clean environment. Reagents and containers used were all subjected to steam sterilization processing. The treatment conditions were as follows: a temperature was 121° C., a pressure was 103.4 KPa, and a time was 20 min; sterile feed and sample collecting pump were adopted for high-pressure crushing.

Figure 2A:
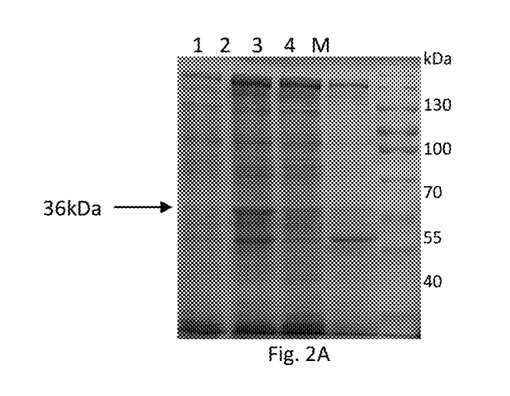
FIG. 2A is SDS-PAGE electrophoresis identification of protein expression under the condition of a second embodiment, M is a pre-dyed standard protein molecular weight, lane 1 is an induced pET/BL21 whole strain, lane 2 is an induced PFL/BL21 whole strain, lane 3 is an induced PFL/BL21 lysate supernatant, and lane 4 is an induced PFL/BL21 lysate precipitate.
Figure 2B:
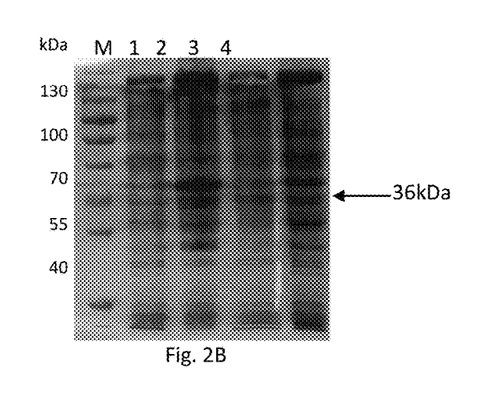
FIG. 2B is SDS-PAGE electrophoresis identification of protein expression under the condition of a third embodiment, M is a pre-dyed standard protein molecular weight, lane 1 is an induced pET/BL21 whole strain, lane 2 is an induced PFL/BL21 whole strain, lane 3 is an induced PFL/BL21 lysate precipitate, and lane 4 is an induced PFL/BL21 lysate supernatant.

(4) The expression of the recombinant strain PFL/BL21 under two conditions was analyzed, wherein 80 μL induced PFL/BL21 whole strain and 80 μL lysate supernatant and 80 μL precipitate thereof in the foregoing second embodiment were taken and added with 20 μL 5*SDS protein loading buffer, boiled at 100° C. for 10 min, and identified by SDS-PAGE, wherein the control was induced pET/BL21 whole strain, to obtain FIG. 2A. 80 μL induced PFL/BL21 whole strain and 80 μL lysate supernatant and 80 μL precipitate thereof in the foregoing third embodiment were taken and added with 20 μL 5*SDS protein loading buffer, boiled at 100° C. for 10 min, and identified by SDS-PAGE, wherein the control was induced pET/BL21 whole strain, to obtain FIG. 2B. It could be seen from FIGS. 2A and 2B that, compared with the control strain, the induced PFL/BL21 whole strain and the lysate supernatant and precipitate lanes thereof showed obvious target bands at 36 KD, and the amount of soluble target protein in the lysate supernatant was about 50%-60% of the total target protein. Under the two expression conditions, although the total protein contents were slightly different, the expressed target protein contents were basically stable.

The expression of the adaptor protein was induced by the recombinant expression strain PFL/BL21 according to the method in the embodiment. The recombinant strain after the induced expression are subjected to high pressure cracking, and a lysate supernatant was taken, thus obtaining an adaptor protein solution.

A nearly same protein expression amount was gained when the recombinant expression strain PFL/BL21 obtained in the embodiment was successive passaged and induced by 30 batches, which mean that stable expression of adaptor protein could be repeatedly operated.

Fifth Embodiment Identification for Expression of Adaptor Protein

Figure 3:
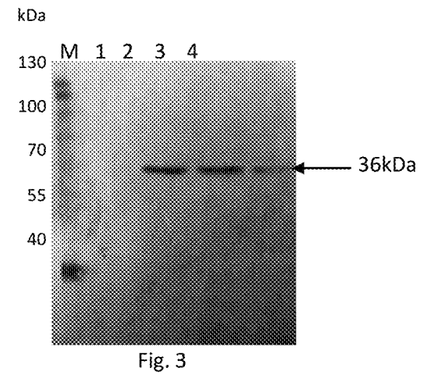
FIG. 3 is a Western-blot identification result of the adaptor protein, wherein M is a pre-dyed standard protein molecular weight, lane 1 is an induced pET/BL21 whole strain, lane 2 is an induced PFL/BL21 whole strain, lane 3 is an induced PFL/BL21 lysate supernatant, and lane 4 is an induced PFL/BL21 lysate precipitate.

In order to identify the adaptor protein, the induced PFL/BL21 whole strain and the lysate supernatant and precipitate thereof were identified by Western-blot by means of a carboxy terminus His-tag protein. The negative control was the induced pET/BL21 whole strain. A specific method was as follows: SDS-PAGE electrophoresis results of each sample were transferred to a nitrocellulose film, and then the transferred film was blocked with a TBST containing 5% BSA at room temperature for 1 h, and washed thrice with TBST buffer at 37° C., and incubated with 1:5000 times diluted mouse anti-His monoclonal antibody (purchased from Abcam, article No. ab15149) for 1 h; then washed thrice with TBST buffer, and incubated with 1:10000 times diluted goat anti-mouse HRP-IgG antibody (horseradish peroxidase-labeled goat anti-mouse IgG antibody, purchased from KPL company, Article No. 510-0183) for 45 min; After the incubation, the antibody was washed thrice with TBST buffer, and then a DAB color reagent kit was used for color development and photographed for preservation. Results were as shown in FIG. 3, wherein an obvious band appeared in the supernatant lane of the induced PFL/BL21 lysate supernatant, proving the successful expression of the adaptor protein.

His (histidine) tag protein was only for the convenience of identification of the expressed protein and did not affect the expression of protein and the functions thereof. In the actual production process, as long as the coding gene of the adaptor protein was inserted into pET32a and then introduced into BL21 (DE3) to screen positive recombinant strain, it can be used to produce the adaptor protein.

Sixth Embodiment Quantitative Analysis of Adaptor Protein

1. Preparation of Purified Carrier

*Lactococcus lactis* IL1403 (The Complete Genome Sequence of the Lactic Acid Bacterium *Lactococcus lactis* ssp. *lactis* IL1403, Genome Res., 10.1101/gr.169701.) was cultured in a fresh GM17 medium at 30° C. for 16 to 18 h, and centrifuged at 8000 rpm for 5 min to collect cells, then a precipitate was washed once with PBS buffer, added with 0.1 mol/L hydrochloric acid, boiled for 30 min, and centrifuged at 8000 rpm for 5 min, then a precipitate was washed thrice with PBS buffer, and finally resuspended with the PBS buffer to obtain a *Lactococcus lactis* skeleton, i.e., the purified carrier. Cell count was conducted on the purified carrier, $2.5*10^9$ purified carriers were counted as one unit.

2. Protein Dissociation

An adaptor protein solution was prepared according to the method in the second embodiment. In 2 mL adaptor protein solution (total protein content of 4.2 mg), excessive purified carrier ($10*10^9$) was added and incubated for 30 min to allow the adaptor protein to completely bind to the purified carriers, and centrifuged at 9000 rpm for 3 min to obtain a supernatant 1 and a precipitate 1, wherein the precipitate 1 contained the purified carrier and a complex thereof with the adaptor protein. The precipitate 1 was resuspended by 400 μL PBS buffer.

SDS (sodium dodecyl sulfate) at a final concentration of 1% was added to a resuspension solution of the precipitate 1 and boiled at 100° C. for 10 min to dissociate the adaptor protein from the purified carrier, and then centrifuged at 12000 rpm for 10 min to harvest a supernatant 2 and a precipitate 2, wherein the precipitate 2 was used to be resuspended with the PBS buffer in a volume equal to the supernatant 2.

3. Protein Dissociation Identification

Figure 4:
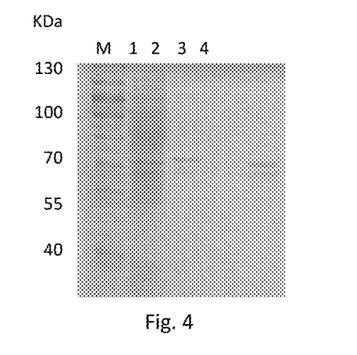
FIG. 4 is an SDS-PAGE identification result of combination and dissociation of an adaptor protein and a purified carrier, wherein M is a pre-dyed standard protein molecular weight, lane 1 is a supernatant 1, lane 2 is a precipitate 1, lane 3 is a precipitate 2, and lane 4 is a supernatant 2.

In order to analyze whether the adaptor protein was completely dissociated from the purified carrier, SDS-PAGE electrophoresis analysis was performed on the supernatant 1, the precipitate 1, the supernatant 2 and the precipitate 2. The results were shown in FIG. 4, and the adaptor proteins after dissociation were all in the supernatant 2 (lane 4).

4. Effective Content Determination of Adaptor Protein

The total protein content in the supernatant 2 was determined by a BCA protein quantification kit, and the result was the total amount of the adaptor protein in 2 mL adaptor protein solution (prepared according to the method in the second embodiment). The test results were shown in Table 3. According to the calculation results, it was found that about 90 μg adaptor protein was finally obtained per ml of the LB medium.

For ease of use, the concentration of the adaptor protein in the adaptor protein solution was adjusted to 50 μg/mL by a sterile PBS buffer.

Figure 11:
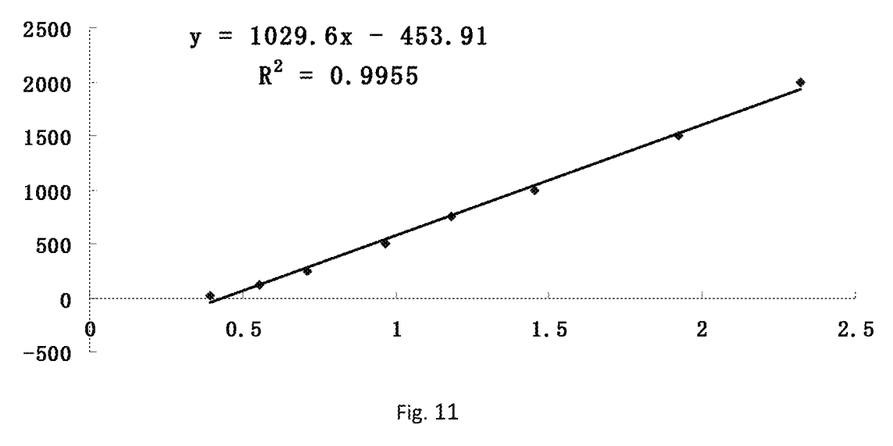
FIG. 11 is a standard curve of a BCA protein quantitative detection result.

Table 3 shows the quantitative detection results of BCA protein. See FIG. 11 for a standard curve thereof.

TABLE 3

| Sample | OD value | Protein content μg/mL |
|---|---|---|
| Standard curve sample 1 | 2.319 | 2000 |
| Standard curve sample 2 | 1.924 | 1500 |
| Standard curve sample 3 | 1.454 | 1000 |
| Standard curve sample 4 | 1.181 | 750 |
| Standard curve sample 5 | 0.967 | 500 |
| Standard curve sample 6 | 0.709 | 250 |
| Standard curve sample 7 | 0.554 | 125 |
| Standard curve sample 8 | 0.392 | 25 |
| Supernatant 2 | 0.886 | 458.32 |
| Supernatant 2 | 0.875 | 446.99 |

The average protein content in the supernatant 2 was 452.65 μg/ml, and the total content of the 2 mL adaptor protein was 181.06 μg (452.65 μg/mL*0.4 mL).

Seventh Embodiment Purification and Concentration of Inactivated O-Type FMDV

1. Antigen Preparation

An O-type FMDV was proliferated by BHK cells, and then the culture was repeatedly freeze-thawed and clarified, to obtain an inactivated O-type FMDV antigen. An antigen titer was $10^{8.5}$ $TCID_{50}$/mL, a 146S content was 5.6 μg/mL, and a total protein concentration was 716.4 μg/mL.

2. Purification and Concentration of Inactivated O-Type FMDV Antigen (1) Under an aseptic condition, an adaptor protein concentration in an adaptor protein solution (prepared according to the method in the fourth embodiment) was adjusted to 50 μg/mL, and then added to an inactivated O-type FMDV antigen to be purified with a ratio of addition as follows: 50 μg adaptor protein was added in every 5 mL O-type inactivated FMDV antigen with a titer of $10^{8.5}$ $TCID_{50}$/mL, and then the mixture was mixed evenly and sufficiently.

(2) The above mixture was placed in a shaker at 25° C. and a rotating speed of 150 rpm, and incubated for 50 min with shaking, so that the inactivated O-type FMDV antigen completely bound to the adaptor protein.

(3) Under an aseptic condition, a purified carrier prepared in the sixth embodiment was added with a ratio of addition as follows: $2.5*10^9$ purified carriers were added in every 5 mL inactivated O-type FMDV antigen with a titer of $10^{8.5}$ $TCID_{50}$/mL, and then a mixture was stirred evenly and sufficiently.

(4) The above mixture was placed in a shaker at 25° C. and a rotating speed of 150 rpm, and incubated for 30 min with shaking, so that the adaptor protein bound with the inactivated O-type FMDV antigen completely bound to the purified carrier.

(5) The mixture was centrifuged at 9000 rpm for 5 min under the aseptic condition to obtain a supernatant 3 and a precipitate 3.

The precipitate 3 was the purified inactivated O-type FMDV antigen complex. The inactivated O-type FMDV antigen complex was a complex of the inactivated O-type FMDV antigen, the adaptor protein and a *Lactococcus lactis* skeleton, and the principle of forming the inactivated O-type FMDV antigen complex was that the adaptor protein could specially bind to the inactivated O-type FMDV antigen and the *Lactococcus lactis* skeleton at the same time. Therefore, a final product of the method for purifying and concentrating an inactivated O-type FMDV antigen of the present embodiment was an inactivated O-type FMDV antigen complex, i.e., the precipitate 3.

The precipitate 3 was resuspended by a TE buffer (aqueous solution containing 10 mmol/L Tris-HCL and 50 mmol/L NaCl with a pH of 8.0) 0.1 times the original virus volume (about 0.5 mL).

In the purification process, in order to ensure the complete recovery of the inactivated O-type FMDV antigen, both the *Lactococcus lactis* skeleton and the adaptor protein were excessively added; therefore, the inactivated O-type FMDV purified antigen complex obtained by the method for purifying and concentrating in the embodiment (precipitate 3) also contained a small amount of the *Lactococcus lactis* skeleton and a complex thereof with the adaptor protein.

All the following "inactivated O-type FMDV purified antigen complexes" refer to the precipitate 3.

3. Purification and Concentration Identification of Inactivated O-Type FMDV Antigen In order to verify the object that the inactivated O-type FMDV antigen was purified and concentrated by the method in the embodiment, the supernatant 3 and the precipitate 3 obtained in the embodiment were subjected to SDS-PAGE electrophoresis and Western-blot identification analysis to obtain FIG. 5A and FIG. 5B.

The O-type FMDV inactivating antigen before purification, the precipitate 3, and the supernatant 3 were identified by SDS-PAGE electrophoresis to obtain FIG. 5A. The above-mentioned SDS-PAGE electrophoresis results were subjected to FMDV O-type virus Western-blot identification to obtain FIG. 5B. The specific steps of Western-blot were as follows.

(1) Transfer: after the SDS-PAGE electrophoresis, the Western blot was transferred to a PVDF film (polyvinylidene fluoride film by a wet transfer method, and film transfer conditions were constant pressure 100 V for 45 min.

(2) block: the PVDF film was blocked overnight with a TBST buffer (pH 8.0) containing 5% skim milk at 4° C.

(3) Incubate primary antibody: the above PVDF film was washed and immersed in a bovine 0-type FMDV positive serum (positiveserum was obtained from a bovine immunized with the inactivated O-type FMDV antigen) diluted with 1:40 TBST solution containing 2% BSA, and incubated at 37° C. for 1 h.

(4) Wash: the PVDF film was taken out and rinsed four times by the TBST buffer, and each rinsing lasted for 8 min.

(5) Incubate secondary antibody: the PVDF film was immersed in a goat-anti-bovine IgG-HRP (horseradish peroxidase-labeled goat-anti-bovine IgG antibody, purchased from KPL company, Article No. 5210-0619, and a dilution degree of 1:4 000) diluted by a TBST solution containing 2% BSA and incubated at 37° C. for 45 min.

(6) Wash same as (4): color development was conducted by a DAB color reagent kit.

The size of the antigen was approximately 25 KDa. Results of FIG. 5A and FIG. 5B showed that after purification, antigen bands were not found in the supernatant 3 by the SDS-PAGE and Western-blot, but were mainly enriched in the precipitate 3, i.e., the inactivated O-type FMDV purified antigen complex; moreover, it could be seen from the figures that most of non-antigen proteins were removed after purification, and the antigen purity was significantly improved.

4. Determination of the Antigen Recovery Efficiency for Inactivated O-Type FMDV Antigen (1) In order to detect the antigen recovery efficiency of the method in the embodiment, an antibody-coated plate provided by an FMDV O-type antibody blocking ELISA kit (Lanzhou Veterinary Research Institute) was used to detect the antigen contents in the inactivated 0-type FMDV antigen (title 1 in the embodiment) and in the supernatant 3. Data detection results showed that the antigen remained in the supernatant 3 was lower than that of the inactivated O-type FMDV antigen diluted to $2^8$ (256) times, indicating that the remained virus in the supernatant 3 was less than 1% of the original antigen, i.e., the antigen recovery efficiency of the method for purifying in the present embodiment was higher than 99%.

(2) In order to analyze the purity in the purified antigen complex, the precipitate 3 was dissociated by the method in the title 2 of the embodiment, and total protein contents of a dissociated supernatant of the precipitate 3 and the unpurified inactivated O-type FMDV antigen (the title 1 in the embodiment) were determined using a BCA protein quantification kit. The total protein content determined in the inactivated O-type FMDV antigen was 3582 μg (716.4 μg/mL*5 mL), and the total protein in the dissociated supernatant of the precipitate 3 was 245 μg (490 μg/mL*0.5 mL), so the impurity protein removal rate=[1−(245/3582)]*100%, which was higher than 90%; according to the calculation that the antigen recovery efficiency was higher than 99%, the 146s content in the purified antigen complex (precipitate 3) was about 28 μg (5.6 μg/mL*5 mL*99%), the antigen purity in the purifiedantigen complex=(28/245)*100%, and the antigen purity was higher than 10%.

Eighth Embodiment Purification and Concentration of Inactivated A-Type FMDV Antigen The method for purifying and concentrating an inactivated A-type FMDV antigen includes the following steps.

1. Antigen preparation: an A-type FMDV was proliferated by BHK cells, and then the culture was repeatedly freeze-thawed and clarified to obtain an inactivated A-type FMDV antigen. An antigen titer was $10^{8.3}$ TCID$_{50}$/mL, a 146S content was 5.2 μg/mL, and a total protein concentration was 680 μg/mL.

2. Purification and Concentration of Inactivated A-Type FMDV Antigen (1) Under an aseptic condition, an adaptor protein concentration in an adaptor protein solution (prepared according to the method in the fourth embodiment) was adjusted to 50 μg/mL, and then added to an inactivated A-type FMDV antigen to be purified with a ratio of as follows: 50 μg adaptor protein was added in every 5 mL inactivated O-type FMDV antigen with a titer of $10^{8.3}$ TCID$_{50}$/mL, and then a mixture was mixed evenly and sufficiently.

(2) The above mixture was placed in a shaker at 25° C. and a rotating speed of 150 rpm, and incubated for 55 min with shaking, so that the Inactivated A-type FMDV antigen completely bound to the adaptor protein.

(3) Under an aseptic condition, a purified carrier (prepared in the sixth embodiment) was added with a ratio of addition as follows: 2.5*$10^9$ purified carriers were added in every 5 mL inactivated A-type FMDV antigen with a titer of $10^{8.3}$ TCID$_{50}$/mL, and then a mixture was stirred evenly and sufficiently.

(4) The above mixture was placed in a shaker at 25° C. and a rotating speed of 150 rpm, and incubated for 30 min with shaking, so that the adaptor protein bound with the inactivated A-type FMDV antigen completely bound to the purified carrier.

(5) The mixture was centrifuged at 9000 rpm for 5 min under the aseptic condition to obtain a supernatant 4 and a precipitate 4.

The precipitate 4 was the inactivated A-type FMDV purified antigen complex. The precipitate was resuspended by a TE buffer (aqueous solution containing 10 mmol/L Tris-HCL and 50 mmol/L NaCl with a pH of 8.0) 0.1 times the original virus volume (about 0.5 mL). The inactivated A-type FMDV purified antigen complex was a complex of the inactivated A-type FMDV antigen, the adaptor protein and a *Lactococcus lactis* skeleton, and the principle of forming the inactivated A-type FMDV antigen complex was that the adaptor protein could specially bind to the A-type FMDV antigen and the *Lactococcus lactis* skeleton at the same time. Therefore, a final product of the method for purifying and concentrating an inactivated A-type FMDV antigen of the present embodiment was an inactivated A-type FMDV purified antigen complex, i.e., the precipitate 4.

During the purification process, in order to ensure the complete recovery of the inactivated A-type FMDV antigen, both the *Lactococcus lactis* skeleton and the adaptor protein were excessively added; therefore, the Inactivated A-type FMDV antigen complex (precipitate 4) also contained a small amount of the *Lactococcus lactis* skeleton and a complex thereof with the adaptor protein.

3. Purification and Concentration Identification of Inactivated A-Type FMDV Antigen In order to verify the object that the inactivated A-type FMDV antigen was purified and concentrated by the method in the embodiment, the inactivated A-type FMDV antigen before purification, the supernatant 4 and the precipitate 4 obtained in the title 2 of the embodiment were subjected to SDS-PAGE electrophoresis and Western-blot identification analysis to obtain FIG. 6A and FIG. 6B.

The Western-blot procedures were the same as that in the fourth embodiment except that the primary antibody was replaced with an A-type FMDV positive serum. A preparation method of the A-type FMDV positive serum was as follows: The inactivated A-type FMDV was used to immunize a bovine, and blood was taken from the bovine with qualified antibody titer, and the positive serum was obtained after separation.

Results of FIG. 6A and FIG. 6B showed that antigen bands were not found in the in the supernatant 4, but were mainly enriched in the precipitate 4, i.e., the inactivated A-type FMDV purified antigen complex, and a size of the antigen was approximately 25 KDa. It could be seen from the figures that most of non-antigen proteins were removed after purification, and the antigen purity was significantly improved.

4. Determination of the Antigen Recovery Efficiency for Inactivated A-Type FMDV Antigen (1) In order to detect the antigen recovery efficiency of the method in the embodiment, an antibody-coated plate provided by an A-type FMDV antibody blocking ELISA kit (Lanzhou Veterinary Research Institute) was used to detect the antigen contents in the inactivated A-type FMDV antigen and the supernatant 4. Data detection result results showed that the antigen remained in the supernatant 4 was lower than that of the inactivated A-type FMDV antigen diluted by $2^8$(256) times, indicating that the virus residue in the supernatant 4 was less than 1% of the original virus antigen content, i.e., the antigen recovery efficiency of the method for purifying and concentrating in the present embodiment was higher than 99%.

(2) In order to analyze the antigen purity in the inactivated A-type FMDV antigen complex, the precipitate 4 was dissociated by the method in the title 2 of the third embodiment, and total protein contents of a dissociated supernatant of the precipitate 4 and the unpurified inactivated A-type FMDV were determined using a BCA protein quantification kit. The total unpurified protein content determined was 3400 μg (680 μg/mL*5 mL), and the total protein in the precipitate 4 was 228 μg (456 μg/mL*0.5 mL), so the impurity protein removal rate=[1−(228/3400)]*100%, which was higher than 90%; according to the calculation that the antigen recovery efficiency was higher than 99%, the 146s content in the inactivated A-type FMDV antigen complex (precipitate 4) was about 26 μg (5.2 μg/mL*5 mL), the antigen purity in the inactivated A-type FMDV purified antigen complex=(26/228)*100%, and the antigen purity was higher than 10%.

Ninth Embodiment Purification and Concentration of Inactivated Asia1-Type FMDV Antigen 1. Antigen preparation: an Asia1-type FMDV was proliferated by BHK cells, and then the culture was repeatedly freeze-thawed and clarified to obtain an Asia1-type FMDV. An antigen titer was $10^{8.2}$ TCID$_{50}$/mL, a 146S content was 5.3 μg/mL, and a total protein concentration was 658 μg/mL.

2. Purification and Concentration of Inactivated Asia1-Type FMDV Antigen (1) Under an aseptic condition, an adaptor protein concentration in an adaptor protein solution (prepared according to the method in the fourth embodiment) was adjusted to 50 μg/mL, and then added to the inactivated Asia1-type FMDV antigen to be purified with a ratio of as follows: 50 μg adaptor protein was added in every 5 mL inactivated Asia1-type FMDV antigen with a titer of $10^{8.2}$ TCID$_{50}$/mL, and then a mixture was mixed evenly and sufficiently.

(2) The above mixture was placed in a shaker at 25° C. and a rotating speed of 150 rpm, and incubated for 45 min with shaking, so that the FMDV inactivated antigen completely bound to the adaptor protein.

(3) Under an aseptic condition, a purified carrier prepared in the sixth embodiment was added with in a ratio of addition as follows: 2.5*10$^9$ purified carriers were added in every 5 mL inactivated Asia1-type FMDV antigen with a titer of $10^{8.2}$ TCID$_{50}$/mL, and then a mixture was stirred evenly and sufficiently.

(4) The above mixture was placed in a shaker at 25° C. and a rotating speed of 150 rpm, and incubated for 30 min with shaking, so that the adaptor protein bound with the inactivated Asia1-type FMDV antigen completely bound to the purified carrier.

(5) The mixture was centrifuged at 9000 rpm for 5 min under the aseptic condition to obtain a supernatant 5 and a precipitate 5.

The precipitate 5 was the inactivated Asia1-type FMDV purified antigen complex. The precipitate was resuspended by a TE buffer 0.1 times the original virus volume (about 0.5 mL). The inactivated Asia1-type FMDV purified antigen complex was a complex of the inactivated Asia1-type FMDV antigen, the adaptor protein and a *Lactococcus lactis* skeleton, and the principle of forming the inactivated Asia1-type FMDV purified antigen complex was that the adaptor protein could specially bind to the inactivated Asia1-type FMDV antigen and the *Lactococcus lactis* skeleton at the same time. Therefore, a final product of the method for purifying and concentrating an inactivated Asia1-type FMDV antigen of the present embodiment was an inactivated Asia1-type FMDV antigen, i.e., the precipitate 5.

During the purification process, in order to ensure the complete recovery of the inactivated Asia1-type FMDV antigen, both the *Lactococcus lactis* skeleton and the adaptor protein were excessively added; therefore, the inactivated Asia1-type FMDV antigen complex (precipitate 5) also contained a small amount of the *Lactococcus lactis* skeleton and a complex thereof with the adaptor protein.

3. Purification and Concentration Identification of Inactivated Asia1-Type FMDV Antigen In order to verify the object that the inactivated Asia1-type FMDV antigen was purified and concentrated by the method in the embodiment, the supernatant 5 and the precipitate 5 obtained in the embodiment were subjected to SDS-PAGE electrophoresis and Western-blot identification analysis to obtain FIG. 7A and FIG. 7B.

The Western-blot procedures were the same as that in the fourth embodiment except that the primary antibody was replaced with a bovine Asia1-type FMDV positive serum. A preparation method of the bovine Asia1-type FMDV positive serum was as follows: The inactivated A sia1-type FMDV was used to immunize a bovine, and blood was taken from the bovine with qualified antibody titer, and the positive serum was obtained after separation.

Results of FIG. 7A and FIG. 7B showed that antigen bands were not found in the in the supernatant 5, but were mainly enriched in the precipitate 5, i.e., the inactivated Asia1-type FMDV antigen complex, and a size of the antigen was approximately 25 KDa; moreover, it could be seen from the figures that most of hybrid proteins were removed after purification, and the antigen purity was significantly improved.

4. Determination of Antigen Recovery Efficiency for Inactivated Asia1-Type FMDV Antigen (1) In order to detect the antigen recovery efficiency of purifying and concentrating the inactivated antigen by the method in the embodiment, an antibody-coated plate provided by an Asia1-type FMDV antibody blocking ELISA kit (Lanzhou Veterinary Research Institute) was used to detect the antigen contents in the inactivated Asia1-type FMDV antigen and the supernatant 5. Data detection result results showed that the antigen residue in the supernatant 5 was lower than that of the inactivated Asia1-type FMDV antigen diluted by $2^7$(128) times, indicating that the virus residue after purification was less than 1% of the original virus antigen content; therefore, the antigen recovery efficiency was higher than 99%.

(2) In order to analyze the antigen purity in the inactivated Asia1-type FMDV antigen complex, the precipitate 5 was dissociated by the method in the title 2 of the third embodiment, and total protein contents of a dissociated supernatant of the precipitate 5 and the unpurified inactivated Asia1-type FMDV antigen were determined using a BCA protein quantification kit. The total unpurified protein content determined was 3290 μg (658 μg/mL*5 mL), and the total protein in the precipitate 5 was 208 μg (416 μg/mL*0.5 mL), so the impurity protein removal rate=[1−(208/3290)]*100%, which was higher than 90%; according to the calculation that the antigen recovery efficiency was higher than 99%, the 146s content in the inactivated Asia1-type FMDV antigen complex (precipitate 5) was about 26.5 μg (5.3 μg/mL*5 mL), the antigen purity in the inactivated Asia1-type FMDV antigen complex (precipitate 5)=(26.5/208)*100%, and the antigen purity was higher than 10%.

Tenth Example Immunogenicity of Inactivated FMDV Purified Antigen

An inactivated Asia1-type FMDV antigen (title 1 in the ninth embodiment) and an inactivated Asia1-type FMDV purified antigen complex (precipitate 5 in the title 2 of the ninth embodiment) were respectively diluted to a 146S concentration of 5.3 μg/mL by a TE buffer (containing 10 mmol/L Tris-HCL and 50 mmol/L NaCl with a pH of 8.0) and containing about $5*10^8$ purified carriers prepared in the third embodiment, then the mixture was mixed with a 206 adjuvant (purchased from Seepic of France) according to a volume ratio of 46 to 54, and emulsified, so as to respectively prepare an Asia1-type inactivated vaccine and a control vaccine thereof.

An inactivated A-type FMDV antigen (title 1 in the eighth embodiment) and an inactivated A-type FMDV purified antigen complex (precipitate 4 in the title 2 of the eighth embodiment) were respectively diluted to a 146S concentration of 5.2 μg/mL by a TE buffer (containing 10 mmol/L Tris-HCL and 50 mmol/L NaCl with a pH of 8.0) and containing about $5*10^8$ purified carriers prepared in the third embodiment, then the mixture was mixed with the 206 adjuvant (purchased from Seepic of France) according to a volume ratio of 46 to 54, and emulsified, so as to respectively prepare an A-type inactivated vaccine and a control vaccine thereof.

An inactivated O-type FMDV antigen (title 1 in the seventh embodiment) and an inactivated 0-type FMDV purified antigen complex (precipitate 3 in the title 2 of the seventh embodiment) were respectively diluted to a 146S concentration of 5.6 μg/mL by a TE buffer (aqueous solution containing 10 mmol/L Tris-HCL and 50 mmol/L NaCl with a pH of 8.0) and containing about $5*10^8$ purified carriers prepared in the sixth embodiment, then the mixture was mixed with the 206 adjuvant (purchased from Seepic of France) according to a volume ratio of 46 to 54, and emulsified, so as to respectively prepare an O-type inactivated vaccine and a control vaccine thereof.

An adaptor protein solution was mixed with the purified carriers according to the method in the title 2 of the seventh embodiment, and then incubated; other conditions remained unchanged excluding not adding the inactivated FMDV antigen, a precipitate was taken and diluted with a TE buffer (aqueous solution containing 10 mmol/L Tris-HCL and 50 mmol/L NaCl with a pH of 8.0) to contain $5*10^8$ purified carriers prepared in the sixth embodiment, and then the mixture was mixed with the 206 adjuvant (purchased from Seepic of France) according to a volume ratio of 46 to 54, and emulsified, so as to prepare a control vaccine 1.

Control vaccine 2: aqueous solution containing 10 mmol/L Tris-HCL and 50 mmol/L NaCl with a pH of 8.0.

See Table 1 for a serial number of each vaccine and the antigen contained.

TABLE 1

Serial Number of Vaccine and Antigen Contained

| Vaccine name | Antigen |
| --- | --- |
| Asia1-type inactivated vaccine | inactivated Asia1-type FMDVpurifiedantigen complex |
| Asia1-type inactivated control vaccine | inactivated Asia1-type FMDV antigen |
| A-type inactivated vaccine | inactivated A-type FMDV purified antigen complex |
| A-type inactivated control vaccine | inactivated A-type FMDV antigen |
| O-type inactivated vaccine | inactivated O-type FMDV purified antigen complex |
| O-type inactivated control vaccine | inactivated O-type FMDV antigen |
| Control vaccine 1 | Complex of purified carrier and adaptor protein |
| Control vaccine 2 | TE (10 mmol/L Tris-HCL, 50 mmol/L NaCl, pH 8.0) buffer |

1) Immune effect experiment 80 healthy piglets of 40 to 45 days old with a negative antibody to foot-and-mouth disease were randomly divided into eight groups according to the method in Table 2, and immunized by neck muscle injection with an immunizing dose of 2 ml/piglet, and vaccines of each group were shown in Table 2.

Figure 8:
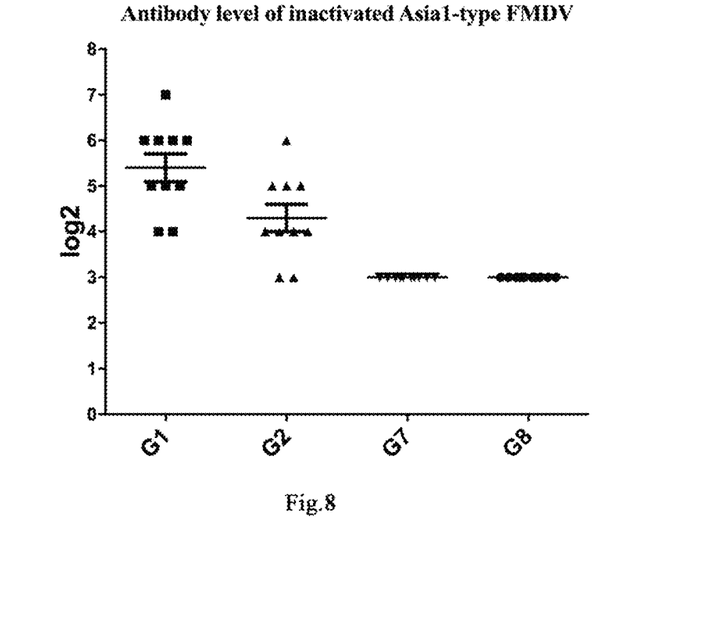
FIG. 8 is an ELISA test result of 28d antibody level blocking of an animal immunized with an Asia1-type FMDV inactivated vaccine.
Figure 9:
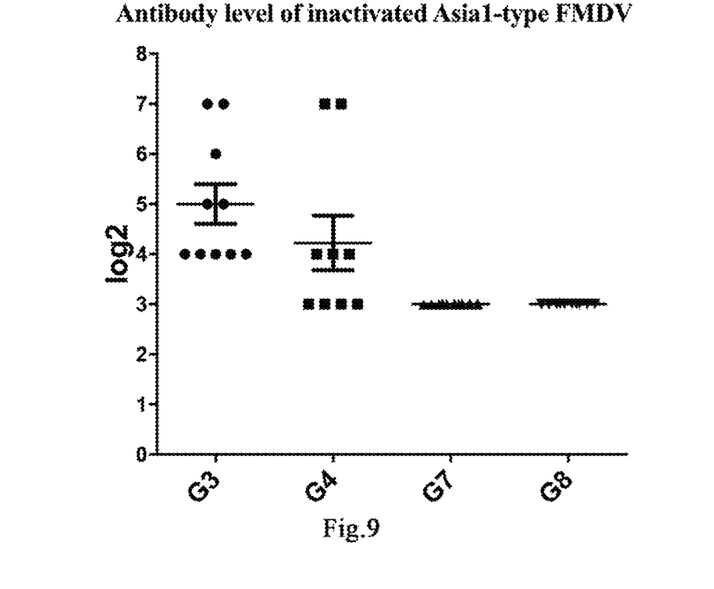
FIG. 9 is an ELISA test result of 28d antibody level blocking of an animal immunized with an A-type FMDV inactivated vaccine antigen.
Figure 10:
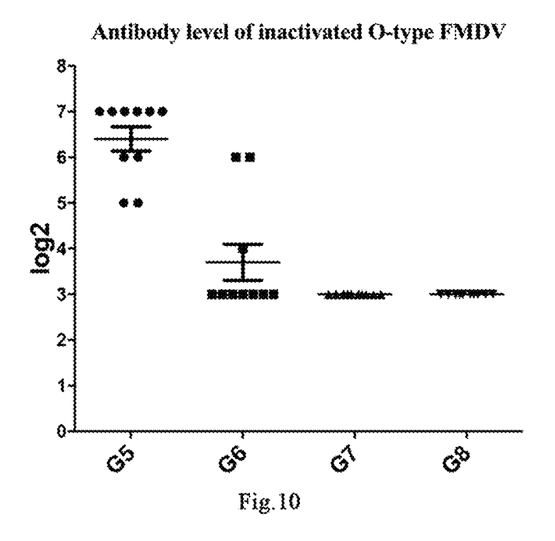
FIG. 10 is an ELISA test result of 28d antibody level blocking of an animal immunized with an 0-type FMDV inactivated vaccine.

Blood was collected 28 days after immunization, serum was separated, a liquid-phase blocking antibody level was detected, and the immunogenicity of an antigen complex was evaluated. It could be seen from FIGS. 8, 9 and 10 that the antibody levels of the control vaccine 1 (G7 Group) and the control vaccine 2 (G8 Group) immune groups were negative, which indicated that the purified carriers, the adaptor protein and the TE buffer introduced in the purification process could not affect the antibody levels of the vaccines; the antibody levels of three subtype FMDV antigen complexes after purification were significantly higher than those made of purified antigens, wherein an immune group (G1) of the inactivated Asia1-type FMDV antigen was about higher than the average antibody level of a control group (G2) thereof by one titer, an immune Group (G3) of the inactivated A-type FMDV antigen complex was higher than the average antibody level of a control group (G4) by about 0.7 titer, and an immune group (G5) of the inactivated O-type FMDV antigen complex was higher than the average antibody level of a control group (G6) by about 2 titers. The increasing antibody levels of the three subtype inactivated FMDV purifiedantigen complexes were inconsistent, which may be possibly related to the original immunogenicity of each antigen or the difference among animals, and did not affect the overall increasing trend of the antibodies. This indicated that the purified complex prepared by the purifying and concentrating method in this invention could be used for preparing monovalent or multivalent foot-and-mouth disease vaccines with high antigen purity and significant immune effect.

TABLE 2

Immune Groups

| Group | Vaccine name |
|---|---|
| G1 | Asia1-type inactivated vaccine |
| G2 | Asia1-type inactivated control vaccine |
| G3 | A-type inactivated vaccine |
| G4 | A-type inactivated control vaccine |
| G5 | O-type inactivated vaccine |
| G6 | O-type inactivated control vaccine |
| G7 | Control vaccine 1 |
| G8 | Control vaccine 2 |

(2) Side reaction

An immune stress response of the piglets in G1 to G8 groups after immunization was observed and recorded immediately, including body temperature, feeding, mental state, etc., and a growth status of the piglets (feeding, body weight, coat, etc.) within 28 days after immunization was observed and recorded. The results showed that all of the body temperatures and feeding of the G1, G3, G5 and G7 groups and the G8 control group after immunization were normal, and the growth conditions were good. One piglet showed a hyperactive stress for 0.5 h after immunization respectively in the G2 and G4 groups, one piglet in G2 group, and two piglets in G4 and two piglets in G6 showed stress reactions such as transient hyperthermia and loss of appetite. The result showed that the stress response to the vaccines immunized in the G1, G3 and G5 groups was significantly reduced due to the improvement of the purity of the FMDV antigen thereof. The G7 control group did not show any obvious abnormal reaction until the end of detection after immunization, which indicated that the purified carriers and the adaptor protein introduced in the purification process could not bring toxic or side effects to the organism and could not affect the normal growth of the organism.

What is claimed is:

1. A method for purifying and concentrating inactivated foot-and-mouth disease virus, comprising the following steps of:
   (1) adding an adaptor protein with an amino acid sequence as shown in SEQ ID NO: 2 into the inactivated foot-and-mouth disease virus, mixing evenly, and incubating;
   (2) adding a purified carrier, mixing evenly, and incubating the mixture, the purified carrier being a *Lactococcus lactis* skeleton;
   (3) centrifuging and obtaining a precipitate.

2. The method for purifying and concentrating the inactivated foot-and-mouth disease virus according to claim 1, wherein the incubation conditions in step (1) are as follows: an incubating temperature is 20 to 25° C., and an incubating time is 45 min to 60 min.

3. The method for purifying and concentrating an inactivated foot-and-mouth disease virus according to claim 1, wherein the incubating conditions in step (2) are as follows: an incubating temperature is 20 to 25° C., and an incubating time is 25 min to 35 min.

4. The method for purifying and concentrating an inactivated foot-and-mouth disease virus according to claim 3, wherein an adding ratio of the adaptor protein is as follows: 40 to 60 µg adaptor protein is added into $10^{8.7}$ $TCID_{50}$-$10^{9.2}$ $TCID_{50}$ inactivated foot-and-mouth disease virus.

5. The method for purifying and concentrating an inactivated foot-and-mouth disease virus according to claim 4, wherein an adding ratio of the purified carrier is as follows: $2.4*10^9$ to $2.6*10^9$ purified carriers are added into $10^{8.7}$ $TCID_{50}$-$10^{9.2}$ $TCID_{50}$ inactivated foot-and-mouth disease virus.

6. The method for purifying and concentrating an inactivated foot-and-mouth disease virus according to claim 5, wherein the adaptor protein is obtained through induced expression of a recombinant *E. coli* carrying a coding gene of the adaptor protein.

7. The method for purifying and concentrating an inactivated foot-and-mouth disease virus according to claim 6, wherein the recombinant *E. coli* is obtained through inserting the coding gene of the adaptor protein into an expression vector pET32a(+) with Nde I and Xho I enzyme digestion sites, and then transforming into colibacillus.

8. The method for purifying and concentrating an inactivated foot-and-mouth disease virus according to claim 7, wherein the recombinant *E. coli* is cultured for 1 to 2 h under 35 to 37° C., 2 to 4 h under 24 to 26° C., and stood for 10 to 20 min under 15 to 17° C., and then isopropyl thiogalactoside with a final concentration of 0.1 to 0.3 mmol/L is added to inductively culture the mixture for 18 to 22 h under 15 to 17° C., so as to obtain the adaptor protein.

9. The method for purifying and concentrating inactivated foot-and-mouth disease virus according to claim 1, wherein the *Lactococcus lactis* skeleton is obtained through boiling the *Lactococcus lactis* with hydrochloric acid and washing.

\* \* \* \* \*

SEQUENCE LISTING

```
<160> NUMBER OF SEQ ID NOS: 4

<210> SEQ ID NO 1
<211> LENGTH: 957
<212> TYPE: DNA
<213> ORGANISM: Artificial Sequence
<220> FEATURE:
<223> OTHER INFORMATION: It is synthesized.

<400> SEQUENCE: 1
atgactactt ataccgtcaa atctggtgat actctttggg gaatctcaca aagaacaggt      60
tcagcttctt ctacaaattc aggtggttca aacaattccg caagcactac tccaaccact     120
tctgtgacac ctgcaaaacc aacttcacaa acaactgtta aggttaaatc cggagatacc     180
ctttgggcgc tatcagtaaa atataaaact agtattgctc aattgaaaag ttggaatcat     240
ttaagttcag ataccattta tattggtcaa aatcttattg tttcacaatc tgctgctgct     300
tcaaatcctt cgacaggttc aggctcaact gctaccaata actcaaactc gacttcttct     360
aactcaaatg cctcaattca taaggtcgtt aaaggagata ctctctgggg actttcgcaa     420
aaatctggca gcccaattgc ttcaatcaag gcttggaatc atctacgaat aaaaatgcct     480
caattcataa ggtcgttaaa ggagatactc tctgggact tcaattgct tcaatcaagg      540 cttggaatca tttatctagc gatggaatta gtgtcgctca aattcaaagt gcgaataatc     600
ttaaaagtac cattatctac attgtactgc atactatttt atattcaaag tgcgaataat     660
```

```
cttaaaagta ccattatcta cattggtcaa aaacttgtac tggatacctg taacgaaagt    720
accatctatc tgcgtaaata ccagtccaaa gttaaacgcc aataccagtc cgaagtcgac    780
atcattcgcg atgaaatcac cagcgacacc agctacgaaa gcgttggtcg tttcattcgt    840
gacgatgcga aaaacatggt gctgatgaac cgtaagccgg aggatgcggt ttactatggt    900
ctgcgtgcga gcaccgcggg ttgggaaccg cgttgtagct ggggtacccc cgtttaa      957
```

<210> SEQ ID NO 2
<211> LENGTH: 318
<212> TYPE: PRT
<213> ORGANISM: Artificial Sequence
<220> FEATURE:
<223> OTHER INFORMATION: It is synthesized.

<400> SEQUENCE: 2

```
Met Thr Thr Tyr Thr Val Lys Ser Gly Asp Thr Leu Trp Gly Ile Ser
1               5                   10                  15

Gln Arg Thr Gly Ser Ala Ser Ser Thr Asn Ser Gly Gly Ser Asn Asn
            20                  25                  30

Ser Ala Ser Thr Thr Pro Thr Thr Ser Val Thr Pro Ala Lys Pro Thr
        35                  40                  45

Ser Gln Thr Thr Val Lys Val Lys Ser Gly Asp Thr Leu Trp Ala Leu
    50                  55                  60

Ser Val Lys Tyr Lys Thr Ser Ile Ala Gln Leu Lys Ser Trp Asn His
65                  70                  75                  80

Leu Ser Ser Asp Thr Ile Tyr Ile Gly Gln Asn Leu Ile Val Ser Gln
                85                  90                  95

Ser Ala Ala Ala Ser Asn Pro Ser Thr Gly Ser Gly Ser Thr Ala Thr
            100                 105                 110

Asn Asn Ser Asn Ser Thr Ser Ser Asn Ser Asn Ala Ser Ile His Lys
        115                 120                 125

Val Val Lys Gly Asp Thr Leu Trp Gly Leu Ser Gln Lys Ser Gly Ser
    130                 135                 140

Pro Ile Ala Ser Ile Lys Ala Trp Asn His Leu Arg Ile Lys Met Pro
145                 150                 155                 160

Gln Phe Ile Arg Ser Leu Lys Glu Ile Leu Ser Gly Asp Phe Gln Leu
                165                 170                 175

Leu Gln Ser Arg Leu Gly Ile Ile Tyr Leu Ala Met Glu Leu Val Ser
            180                 185                 190

Leu Lys Phe Lys Val Arg Ile Ile Leu Lys Val Pro Leu Ser Thr Leu
        195                 200                 205

Tyr Cys Ile Leu Phe Tyr Ile Gln Ser Ala Asn Asn Leu Lys Ser Thr
    210                 215                 220

Ile Ile Tyr Ile Gly Gln Lys Leu Val Leu Asp Thr Cys Asn Glu Ser
225                 230                 235                 240

Thr Ile Tyr Leu Arg Lys Tyr Gln Ser Lys Val Lys Arg Gln Tyr Gln
                245                 250                 255

Ser Glu Val Asp Ile Ile Arg Asp Glu Ile Thr Ser Asp Thr Ser Tyr
            260                 265                 270

Glu Ser Val Gly Arg Phe Ile Arg Asp Asp Ala Lys Asn Met Val Leu
        275                 280                 285

Met Asn Arg Lys Pro Glu Asp Ala Val Tyr Tyr Gly Leu Arg Ala Ser
    290                 295                 300

Thr Ala Gly Trp Glu Pro Arg Cys Ser Trp Gly Thr Pro Val
305                 310                 315
```

<210> SEQ ID NO 3
<211> LENGTH: 975
<212> TYPE: DNA
<213> ORGANISM: Artificial Sequence
<220> FEATURE:
<223> OTHER INFORMATION: It is synthesized

<400> SEQUENCE: 3

```
atgactactt ataccgtcaa atctggtgat actctttggg gaatctcaca aagaacaggt      60
tcagcttctt ctacaaattc aggtggttca aacaattccg caagcactac tccaaccact     120
tctgtgacac ctgcaaaacc aacttcacaa acaactgtta aggttaaatc cggagatacc     180
ctttgggcgc tatcagtaaa atataaaact agtattgctc aattgaaaag ttggaatcat     240
ttaagttcag ataccattta tattggtcaa aatcttattg tttcacaatc tgctgctgct     300
tcaaatcctt cgacaggttc aggctcaact gctaccaata actcaaactc gacttcttct     360
aactcaaatg cctcaattca taaggtcgtt aaaggagata ctctctgggg actttcgcaa     420
aaatctggca gcccaattgc ttcaatcaag gcttggaatc atctacgaat aaaaatgcct     480
caattcataa ggtcgttaaa ggagatactc tctggggact ttcaattgct tcaatcaagg     540
cttggaatca tttatctagc gatggaatta gtgtcgctca aattcaaagt gcgaataatc     600
ttaaaagtac cattatctac attgtactgc atactatttt atattcaaag tgcgaataat     660
cttaaaagta ccattatcta cattggtcaa aaacttgtac tggatacctg taacgaaagt     720
accatctatc tgcgtaaata ccagtccaaa gttaaacgcc aataccagtc cgaagtcgac     780
atcattcgcg atgaaatcac cagcgacacc agctacgaaa gcgttggtcg tttcattcgt     840
gacgatgcga aaaacatggt gctgatgaac cgtaagccgg aggatgcggt ttactatggt     900
ctgcgtgcga gcaccgcggg ttgggaaccg cgttgtagct ggggtacccc cgttcaccac     960
caccaccacc actaa                                                     975
```

<210> SEQ ID NO 4
<211> LENGTH: 6
<212> TYPE: PRT
<213> ORGANISM: Artificial Sequence
<220> FEATURE:
<223> OTHER INFORMATION: It is synthesized

<400> SEQUENCE: 4

His His His His His His
1               5